United States Patent [19]

Grimmel et al.

[11] Patent Number: 5,382,509
[45] Date of Patent: Jan. 17, 1995

[54] METHOD AND KIT FOR THE DIAGNOSIS OF HUMAN PAPILLOMAVIRUS TYPE 41

[75] Inventors: Margitta Grimmel, Neustadt; Ethel-Michele de Villiers, Hirschberg, both of Germany

[73] Assignee: Behringwerke Aktiengesellschaft, Marburg/Lahn, Germany

[21] Appl. No.: 156,936

[22] Filed: Nov. 23, 1993

Related U.S. Application Data

[60] Continuation of Ser. No. 25,812, Mar. 3, 1993, abandoned, which is a continuation of Ser. No. 840,090, Feb. 24, 1992, abandoned, which is a division of Ser. No. 216,913, Jul. 8, 1988, Pat. No. 5,142,032.

Foreign Application Priority Data

Jul. 11, 1987 [DE] Germany ............................ 3722968

[51] Int. Cl.⁶ ........................ C12Q 1/70; C07H 21/04
[52] U.S. Cl. .......................................... 435/5; 435/6; 536/23.72; 536/24.32; 935/78
[58] Field of Search ............. 435/5, 6; 536/23.72, 536/24.32; 935/77, 78

References Cited

U.S. PATENT DOCUMENTS

| | | | |
|---|---|---|---|
| 4,849,331 | 7/1989 | Lorincz | 435/5 |
| 4,849,334 | 7/1989 | Lorincz | 435/5 |
| 5,057,411 | 10/1991 | Lancaster | 435/6 |

OTHER PUBLICATIONS

Radloff, R., et al., Proc. Nat. Acad. Sci. 57:1514–1521 (1967).
Southern, E. M., J. Mol. Biol. 98:503–517 (1975).
Messing, J., et al., Proc. Nat. Acad. Sci. 74:3642–3646 (1977).
Birnboim, H. C., et al., Nucleic Acids Research, 7:1513–1523 (1979).
Gissmann, L., et al., Int. J. Cancer 29:143–146 (1982).
Yanisch-Perron, C., et al., Gene 33:103–119 (1985).
Fuchs, P., et al., Journal of Virology 58:626–634 (1986).
Hausen, H., et al., The Papovaviridae 2:245–263 Plenum Publishing Corporation (1987).
Chemical Abstracts 1347705 (V106).
Chemical Abstracts 1936795 (V106).
Grimmel, M., et al. Int. J. Cancer, 41:5–9 (1988).
DeVilliers, E., Journal of Virology 63:4898–4903 (1989).
Hirt, L., et al., Virus Research (submitted 1990).

*Primary Examiner*—Margaret Parr
*Assistant Examiner*—Carla Myers
*Attorney, Agent, or Firm*—Finnegan, Henderson, Farabow, Garrett & Dunner

[57] ABSTRACT

The invention relates to isolation of human papillomavirus type 41, partial characterization of its genome and its cloning in pUC 19. This opens up an access to early diagnosis of skin tumors associated with HPV 41.

2 Claims, 1 Drawing Sheet

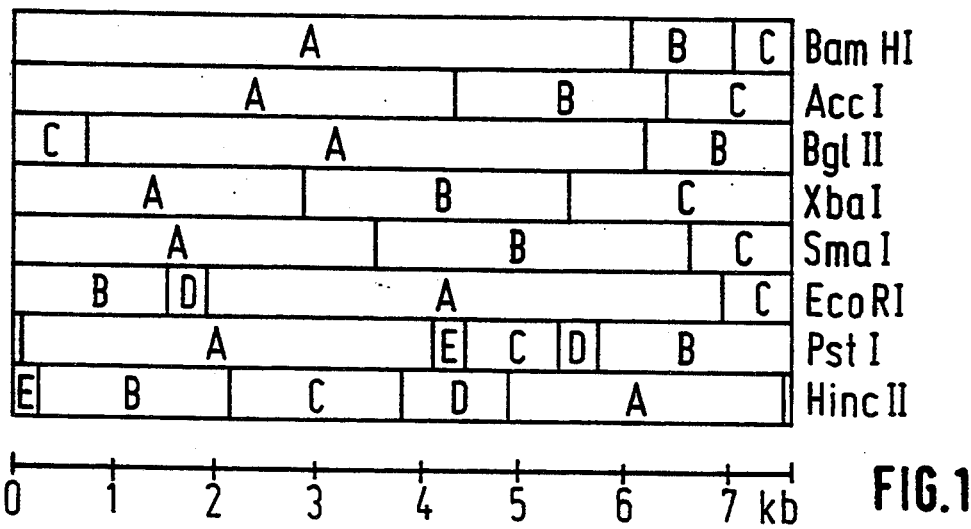
FIG.1
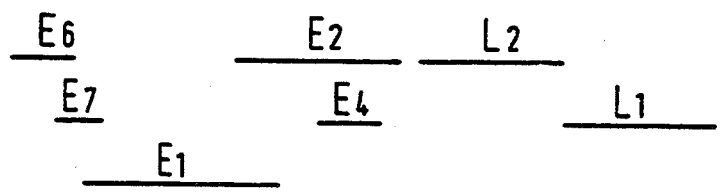
FIG.2
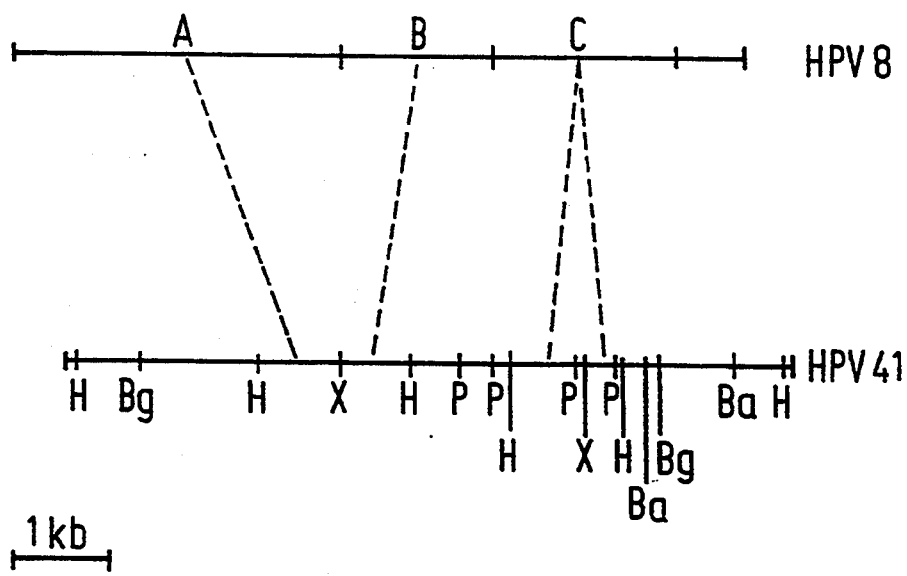

METHOD AND KIT FOR THE DIAGNOSIS OF HUMAN PAPILLOMAVIRUS TYPE 41

This application is a continuation of application Ser. No. 08/025,812, filed Mar. 3, 1993, now abandoned, which is a continuation of application Ser. No. 07/840,090, filed Feb. 24, 1992, now abandoned, which is a division of application Ser. No. 07/216,913 filed Jul. 8, 1988, which issued as U.S. Pat. No. 5,142,032 on Aug. 25, 1992.

Human papillomaviruses (HPV) form a group of about 40 different types (zur Hausen, H. and Schneider, A. (1987), The Papillomaviruses, Howley, P. M. and Salzmann, N. P. (editors), currently being printed). HPV was discovered in connection with benign (warts and condylomata in the genital region) and malignant (carcinomas of the skin and vagina) epithelial neoplasms. Papillomaviruses cannot be multiplied by culture. The use of human papillomavirus type 41DNA (HPV 41DNA) as a diagnostic and the production of expression products, their use as antigens, the isolation of antibodies and the preparation of corresponding diagnostics and therapeutics thus require genetic engineering processes.

The invention is based on the isolation for the first time of HPV 41, a partial characterization of its genome and cloning in pUC 19. This opens up an access to early diagnosis of skin tumors associated with HPV 41.

BRIEF DESCRIPTION OF THE FIGURES

FIG. 1 corresponds to a physical genome chart of the HPV 41 molecule. The single KpnI cleavage site was used to linearize the HPV 41 DNA. HPV 41 DNA was first cleaved from a vector by the restriction enzyme BamHI. The HPV 41 DNA was then digested with the restriction endonucleases AccI, BglII, XbaI, SmaI, EcoRI, PstI and HindII. The fragments produced by endonuclease cleavage were labeled, with "A" designated as the largest fragment produced, "B" the next largest, with each smaller fragment designated by the next letter of the alphabet. The results appear in FIG. 1.

FIG. 2 shows the colinearity of HPV 41 DNA with HPV 8 DNA on the basis of hybridization experiments. The results of the cleavage of the HPV 41 DNA with the restriction endonucleases HindII, BglII, XbaI, PstI, and BamHI compared with the HPV 8 DNA is shown at the bottom of FIG. 2.

The invention is defined in the patent claims. Further embodiments of the invention are described in more detail below.

Cloning of HPV 41 made comparison with 40 other HPV possible. HPV 7, 8, 10, 17, 27, 29, 30 and 33 are distantly related, the colinearity of HPV 41 with HPV 8 having been demonstrated (FIG. 2) and physical genome charts having been drawn up for restriction enzyme cleavages (FIG. 1).

This has thus provided access to testing of neoplasias, in particular carcinomas of the skin, for the occurrence of HPV 41 and, if appropriate, of attempting therapy via antibodies to HPV 41 proteins.

EXAMPLES

1. Isolation of episomal HPV 41DNA

Biopsies from wart tissue from three different body areas of a 15-year old girl were deep-frozen at −70° C. and stored immediately after being obtained. High-molecular DNA was isolated therefrom as described (Gissmann et al. (1982), Int. J. Cancer 29, 143–146). Circular closed double-stranded DNA was obtained from the cellular DNA mentioned in accordance with the method of Radloff et al. (1967) Proc. Nat. Acad. Sci. 57, 1514–1521, about 10 µg of DNA being centrifuged in a 50 Ti rotor (Beckmann Corp.) at 45,000 rpm for 48 hours in CsCl (density 1.56 g/ml) with the addition of 600 µg/ml of ethidium bromide, the fractions with a density of 1.59–1.60 then being collected. Alternatively, episomal HPV 41 DNA of whole DNA from the same biopsy material could be detected in agarose gels stained with ethidium bromide (1% of agarose (Seakem ME) in 40 mM tris-acetate and 2 mM EDTA (pH 7.8)) and isolated therefrom.

2. Cloning of HPV 41 in plasmid pUC 19

The known plasmid pUC 19 (Yanish-Perron et at. (1985), Gene 33, 113–119) was chosen as the cloning vector. Circularly closed double-stranded DNA was cloned in pUC 19 after cleavage with BamHI (Maniatis et al. (1982), Molecular Cloning: a Laboratory Manual; Cold Spring Harbor Laboratory Press, New York). Recombinant clones were identified in the B-galactosidase test (Messing et al. (1977), Proc. Nat. Acad. Sci. USA 74, 3642–3646) and DNA fragments ligated in were analyzed by high-speed DNA extraction (Birnboim, H. L. and Doly. (1979), Nucl. Acids Res. 7, 1513–1523). Two recombinants were obtained, one of which, K 10, contained an insertion of 6.6 kb, and the other of which, K 6, contained an insertion of 0.98 kb. The homology of these cloned sequences is demonstrated by hybridization with episomal DNA from biopsy material.

3. Physical genome charts of HPV 41

HPV 41ONA separated off from the vector by 8amHI cleavage was digested with the restriction endonucleases AccI, BglII, XbaI, SmaI, EcoRI, PstI and HindII and the corresponding physical genome charts were drawn up by generally known methods. The result is summarized in FIG. 1, the sole KpnI cleavage point serving to linearize the HPV 41 molecule.

4. Comparison with other HPV

The DNA of the HPV 41 genome was compared with the DNA's of 40 obtainable types of HPV by means of DNA/DNA hybridization under various stringencies (E. M. Southern (1975), J. Mol. Biol. 98, 503–517). Under conditions of high stringency (melting temperature Tm −20° C.), HPV 41K 10-DNA partly hybridizes with HPV 29-DNA. The DNA of the K 6 clone hybridizes only under low stringency (Tm −40° C.) with HPV 3- and 13-DNA.

The colinearity with HPV 8 on the basis of hybridization experiments is shown in FIG. 2.

Knowing the HPV 8 DNA sequence (Fuchs et al. (1986), J. Virol. 58, 626–634), the open reading frames of HPV 41 are deducible and thus the HPV 41 proteins are obtainable by generally known methods for subcloning clones K 10 and K 6 with subsequent expression in prokaryontic or eukaryontic expression systems.

The plasmids HPV 41 clone K6 and K10 were deposited (in E. coli) on 3.7.1987 under the terms of the Budapest Treaty at the German Collection of Microorganisms Mascheroder Weg 1 b, D-3300 Braunschweig, Federal Republic of Germany, under numbers DSM 4174P (for K6) and DSM 4175P (for K10).

We claim:

1. A diagnostic kit for detecting human papillomavirus type 41 (HPV 41) containing characterized by the restriction enzyme cleavage pattern of FIG. 1 and contained in clones K10 and K6.

2. A method for the diagnosis of HPV 41 infections, which comprises hybridizing the RNA or DNA under investigation with HPV 41 DNA under high stringency hybridizastion stringent conditions, said HPV 41 DNA being characterized by the restriction enzyme cleavage pattern of FIG. 1 and contained in clones K10 and K6.

* * * * *

UNITED STATES PATENT AND TRADEMARK OFFICE
CERTIFICATE OF CORRECTION

PATENT NO. : 5,382,509
DATED : January 17, 1995
INVENTOR(S) : Marita GRIMMEL et al It is certified that error appears in the above-indentified patent and that said Letters Patent is hereby corrected as shown below:

Claim 1, Column 2, line 68, after "containing", insert --HPV 41 DNA--.

Claim 2, Column 3, Line 3, change "HPV 41" to --human papillomavirus type 41 (HPV 41)--.

Claim 2, Column 4, Line 1, delete "stringent".

Signed and Sealed this

Twenty-third Day of May, 1995

*Attest:*

*Attesting Officer*

BRUCE LEHMAN
*Commissioner of Patents and Trademarks*